United States Patent
Abdou

(10) Patent No.: US 8,545,538 B2
(45) Date of Patent: Oct. 1, 2013

(54) DEVICES AND METHODS FOR INTER-VERTEBRAL ORTHOPEDIC DEVICE PLACEMENT

(76) Inventor: M. Samy Abdou, San Diego, CA (US)

(*) Notice: Subject to any disclaimer, the term of this patent is extended or adjusted under 35 U.S.C. 154(b) by 63 days.

(21) Appl. No.: 12/767,573

(22) Filed: Apr. 26, 2010

(65) Prior Publication Data

US 2010/0268281 A1   Oct. 21, 2010

Related U.S. Application Data

(63) Continuation of application No. 11/613,074, filed on Dec. 19, 2006, now Pat. No. 7,704,271.

(60) Provisional application No. 60/751,772, filed on Dec. 19, 2005.

(51) Int. Cl.
  *A61B 17/70* (2006.01)

(52) U.S. Cl.
  USPC .......................................................... 606/266

(58) Field of Classification Search
  USPC ......... 606/246, 256–258, 264–279; 411/380, 411/537
  See application file for complete search history.

(56) References Cited

U.S. PATENT DOCUMENTS

| | | | |
|---|---|---|---|
| 4,309,777 A | 1/1982 | Patil | |
| 4,887,595 A | 12/1989 | Heinig et al. | |
| 5,346,493 A | 9/1994 | Stahurski et al. | |
| 5,358,289 A | 10/1994 | Banker et al. | |
| 5,360,431 A | 11/1994 | Puno et al. | |
| 5,375,823 A | 12/1994 | Navas | |
| 5,385,583 A | 1/1995 | Cotrel | |
| 5,395,371 A | 3/1995 | Miller et al. | |
| 5,415,661 A | 5/1995 | Holmes | |
| 5,423,816 A | 6/1995 | Lin | |
| 5,427,418 A | 6/1995 | Watts | |
| 5,429,639 A | 7/1995 | Judet | |
| 5,443,467 A | 8/1995 | Biedermann et al. | |
| 5,466,237 A | 11/1995 | Byrd, III et al. | |
| 5,468,241 A | 11/1995 | Metz-Stavenhagen et al. | |
| 5,474,555 A | 12/1995 | Puno et al. | |
| 5,476,462 A | 12/1995 | Allard et al. | |
| 5,476,464 A | 12/1995 | Metz-Stavenhagen et al. | |
| 5,480,401 A | 1/1996 | Navas | |
| 5,484,437 A | 1/1996 | Michelson | |

(Continued)

FOREIGN PATENT DOCUMENTS

| | | |
|---|---|---|
| WO | WO 2004/032726 | 4/2004 |
| WO | WO 2004/062482 | 7/2004 |

(Continued)

*Primary Examiner* — Jan Christopher Merene
*Assistant Examiner* — Steven Cotroneo
(74) *Attorney, Agent, or Firm* — Gazdzinski & Associates, PC

(57) ABSTRACT

Within a given spinal segment, the stable vertebral level is identified. Within the lower lumbar spine, that level is most commonly at the sacrum. A bone fastener is rigidly affixed to the stable spinal segment and an interconnecting member is rigidly affixed to the bone fastener so as to form a cantilever construct. Vertebral bodies that exhibit aberrant spinal motion and/or mal-alignment relative to the stable segment are then attached to the interconnecting member using non-rigid bone fastener(s). The motion profile of the dynamic fastener can be varied and may be selected to provide the desired vertebral motion characteristics. The interconnecting member may be rigid or it may be alternatively made rigid parallel to the direction of greatest instability and non-rigid in the other planes.

23 Claims, 9 Drawing Sheets

(56) References Cited

U.S. PATENT DOCUMENTS

| | | |
|---|---|---|
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,284 A * | 3/1998 | Martin ........................ 606/248 |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,830 A | 7/1998 | Farris |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,083,224 A | 7/2000 | Gertzbein et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,912 A | 8/2000 | Cazin et al. |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,549 A | 10/2000 | Keller |
| 6,143,032 A | 11/2000 | Schafer et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,277,122 B1 | 8/2001 | McGahan et al. |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,315,779 B1 | 11/2001 | Morrison et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,402,757 B1 | 6/2002 | Moore et al. |
| 6,440,133 B1 | 8/2002 | Beale et al. |
| 6,440,137 B1 | 8/2002 | Horvath et al. |
| 6,443,956 B1 | 9/2002 | Ray |
| 6,451,021 B1 | 9/2002 | Ralph et al. |
| 6,471,703 B1 | 10/2002 | Ashman |
| 6,471,705 B1 | 10/2002 | Biedermann et al. |
| 6,478,801 B1 | 11/2002 | Ralph et al. |
| 6,485,491 B1 | 11/2002 | Farris et al. |
| 6,485,492 B1 | 11/2002 | Halm et al. |
| 6,485,494 B1 | 11/2002 | Haider |

| Patent | Type | Date | Inventors |
|---|---|---|---|
| 6,488,681 | B2 | 12/2002 | Martin et al. |
| 6,508,818 | B2 | 1/2003 | Steiner et al. |
| 6,511,484 | B2 | 1/2003 | Torode et al. |
| 6,520,962 | B1 | 2/2003 | Taylor et al. |
| 6,527,804 | B1 | 3/2003 | Gauchet et al. |
| 6,530,929 | B1 | 3/2003 | Justis et al. |
| 6,533,786 | B1 | 3/2003 | Needham et al. |
| 6,539,826 | B2 | 4/2003 | Oesterle et al. |
| 6,540,749 | B2 | 4/2003 | Schafer et al. |
| 6,547,790 | B2 | 4/2003 | Harkey, III et al. |
| 6,551,320 | B2 | 4/2003 | Liebermann |
| 6,551,323 | B2 | 4/2003 | Doubler et al. |
| 6,554,831 | B1 | 4/2003 | Rivard et al. |
| 6,554,832 | B2 | 4/2003 | Shluzas |
| 6,554,834 | B1 | 4/2003 | Crozet et al. |
| 6,558,387 | B2 | 5/2003 | Errico et al. |
| 6,562,038 | B1 | 5/2003 | Morrison |
| 6,562,040 | B1 | 5/2003 | Wagner |
| 6,565,565 | B1 | 5/2003 | Yuan et al. |
| 6,565,567 | B1 | 5/2003 | Haider |
| 6,572,618 | B1 | 6/2003 | Morrison |
| 6,582,436 | B2 | 6/2003 | Schlapfer et al. |
| 6,582,466 | B1 | 6/2003 | Gauchet |
| 6,585,740 | B2 | 7/2003 | Schlapfer et al. |
| 6,595,992 | B1 | 7/2003 | Wagner et al. |
| 6,595,993 | B2 | 7/2003 | Donno et al. |
| 6,599,294 | B2 | 7/2003 | Fuss et al. |
| 6,610,063 | B2 | 8/2003 | Kumar et al. |
| 6,613,050 | B1 | 9/2003 | Wagner et al. |
| 6,616,667 | B1 | 9/2003 | Steiger et al. |
| 6,616,669 | B2 | 9/2003 | Ogilvie |
| 6,623,485 | B2 | 9/2003 | Doubler et al. |
| 6,626,347 | B2 | 9/2003 | Ng |
| 6,626,907 | B2 | 9/2003 | Campbell et al. |
| 6,626,908 | B2 | 9/2003 | Cooper et al. |
| 6,635,059 | B2 | 10/2003 | Randall et al. |
| 6,635,060 | B2 | 10/2003 | Hanson et al. |
| 6,645,207 | B2 | 11/2003 | Dixon et al. |
| 6,648,885 | B1 | 11/2003 | Friesem |
| 6,648,887 | B2 | 11/2003 | Ashman |
| 6,648,888 | B1 | 11/2003 | Shluzas |
| 6,652,526 | B1 | 11/2003 | Arafiles |
| 6,652,765 | B1 | 11/2003 | Beaty |
| 6,656,179 | B1 | 12/2003 | Schaefer et al. |
| 6,656,181 | B2 | 12/2003 | Dixon et al. |
| 6,660,004 | B2 | 12/2003 | Barker et al. |
| 6,660,006 | B2 | 12/2003 | Markworth et al. |
| 6,663,632 | B1 | 12/2003 | Frigg |
| 6,663,635 | B2 | 12/2003 | Frigg et al. |
| 6,673,073 | B1 | 1/2004 | Schafer |
| 6,676,661 | B1 | 1/2004 | Benlloch et al. |
| 6,679,833 | B2 | 1/2004 | Smith et al. |
| 6,682,529 | B1 | 1/2004 | Stahurski |
| 6,682,530 | B2 * | 1/2004 | Dixon et al. ................ 606/279 |
| 6,689,133 | B2 | 2/2004 | Morrison et al. |
| 6,689,134 | B2 | 2/2004 | Ralph et al. |
| 6,695,843 | B2 | 2/2004 | Biedermann et al. |
| 6,695,851 | B2 | 2/2004 | Zdeblick et al. |
| 6,699,249 | B2 | 3/2004 | Schlapfer et al. |
| 6,706,045 | B2 | 3/2004 | Lin et al. |
| 6,712,818 | B1 | 3/2004 | Michelson |
| 6,716,213 | B2 | 4/2004 | Shitoto |
| 6,716,214 | B1 | 4/2004 | Jackson |
| 6,716,247 | B2 | 4/2004 | Michelson |
| 6,723,100 | B2 | 4/2004 | Biedermann et al. |
| 6,730,093 | B2 | 5/2004 | Saint Martin |
| 6,730,127 | B2 | 5/2004 | Michelson |
| 6,733,502 | B2 | 5/2004 | Altarac et al. |
| 6,736,816 | B2 | 5/2004 | Ritland |
| 6,736,820 | B2 | 5/2004 | Biedermann et al. |
| 6,740,086 | B2 | 5/2004 | Richelsoph |
| 6,743,231 | B1 | 6/2004 | Gray et al. |
| 6,746,449 | B2 | 6/2004 | Jones et al. |
| 6,755,829 | B1 | 6/2004 | Bono et al. |
| 6,755,835 | B2 | 6/2004 | Schultheiss et al. |
| 6,755,836 | B1 | 6/2004 | Lewis |
| 6,761,723 | B2 | 7/2004 | Butterman et al. |
| 6,767,351 | B2 | 7/2004 | Orbay et al. |
| 6,770,075 | B2 | 8/2004 | Howland |
| 6,778,861 | B1 | 8/2004 | Liebrecht et al. |
| 6,780,186 | B2 | 8/2004 | Errico et al. |
| 6,783,527 | B2 | 8/2004 | Drewry et al. |
| 6,790,209 | B2 | 9/2004 | Beale et al. |
| 6,802,844 | B2 | 10/2004 | Ferree |
| 6,827,719 | B2 | 12/2004 | Ralph et al. |
| 6,830,571 | B2 | 12/2004 | Lenke et al. |
| 6,835,196 | B2 | 12/2004 | Biedermann et al. |
| 6,837,889 | B2 | 1/2005 | Shluzas |
| 6,840,940 | B2 | 1/2005 | Ralph et al. |
| 6,843,791 | B2 | 1/2005 | Serhan |
| 6,857,343 | B1 | 2/2005 | Easterbrooks et al. |
| 6,858,031 | B2 | 2/2005 | Morrison et al. |
| 6,869,432 | B2 | 3/2005 | Schlapfer et al. |
| 6,869,433 | B2 | 3/2005 | Glascott |
| 6,872,208 | B1 | 3/2005 | McBride et al. |
| 6,884,241 | B2 | 4/2005 | Bertranou et al. |
| 6,896,676 | B2 | 5/2005 | Zubok et al. |
| 6,896,677 | B1 | 5/2005 | Lin |
| 6,932,817 | B2 | 8/2005 | Baynham et al. |
| 6,932,820 | B2 | 8/2005 | Osman |
| 6,945,972 | B2 | 9/2005 | Frigg et al. |
| 6,953,462 | B2 | 10/2005 | Liebermann |
| 6,955,677 | B2 | 10/2005 | Dahners |
| 6,958,065 | B2 | 10/2005 | Ueyama et al. |
| 6,964,664 | B2 | 11/2005 | Freid et al. |
| 6,964,665 | B2 | 11/2005 | Thomas et al. |
| 6,964,667 | B2 | 11/2005 | Shaolian et al. |
| 6,966,910 | B2 | 11/2005 | Ritland |
| 6,974,460 | B2 | 12/2005 | Carbone et al. |
| 6,979,334 | B2 | 12/2005 | Dalton |
| 6,981,973 | B2 | 1/2006 | McKinley |
| 6,986,771 | B2 | 1/2006 | Paul et al. |
| 6,989,011 | B2 | 1/2006 | Paul et al. |
| 6,989,044 | B2 | 1/2006 | Zhang et al. |
| 6,991,632 | B2 | 1/2006 | Ritland |
| 7,004,947 | B2 | 2/2006 | Shluzas et al. |
| RE39,035 | E | 3/2006 | Finn et al. |
| 7,008,422 | B2 | 3/2006 | Foley et al. |
| 7,008,424 | B2 | 3/2006 | Teitelbaum |
| 7,011,660 | B2 | 3/2006 | Sherman et al. |
| 7,018,378 | B2 | 3/2006 | Biedermann et al. |
| 7,018,379 | B2 | 3/2006 | Drewry et al. |
| 7,022,122 | B2 | 4/2006 | Amrein et al. |
| 7,029,475 | B2 | 4/2006 | Panjabi |
| RE39,089 | E | 5/2006 | Ralph et al. |
| 7,052,497 | B2 | 5/2006 | Sherman et al. |
| 7,056,321 | B2 | 6/2006 | Pagliuca et al. |
| 7,066,062 | B2 | 6/2006 | Flesher |
| 7,066,937 | B2 | 6/2006 | Shluzas |
| 7,081,116 | B1 | 7/2006 | Carly |
| 7,083,621 | B2 | 8/2006 | Shaolian et al. |
| 7,087,057 | B2 | 8/2006 | Konieczynski et al. |
| 7,090,674 | B2 | 8/2006 | Doubler et al. |
| 7,090,679 | B2 | 8/2006 | Saint-Martin et al. |
| 7,090,680 | B2 | 8/2006 | Bonati et al. |
| 7,094,242 | B2 | 8/2006 | Ralph et al. |
| 7,118,576 | B2 | 10/2006 | Gitis et al. |
| 7,121,755 | B2 | 10/2006 | Schlapfer et al. |
| 7,125,410 | B2 | 10/2006 | Freudiger |
| 7,125,426 | B2 | 10/2006 | Moumene et al. |
| 7,128,743 | B2 | 10/2006 | Metz-Stavenhagen |
| 7,137,985 | B2 | 11/2006 | Jahng |
| 7,141,051 | B2 | 11/2006 | Janowski et al. |
| 7,144,396 | B2 | 12/2006 | Shluzas |
| 7,163,538 | B2 | 1/2007 | Altarac et al. |
| 7,163,539 | B2 | 1/2007 | Abdelgany et al. |
| 7,166,108 | B2 | 1/2007 | Mazda et al. |
| 7,179,261 | B2 | 2/2007 | Sicvol et al. |
| 7,186,255 | B2 | 3/2007 | Baynham et al. |
| 7,188,626 | B2 | 3/2007 | Foley et al. |
| 7,207,991 | B2 | 4/2007 | Michelson |
| 7,207,992 | B2 | 4/2007 | Ritland |
| 7,211,085 | B2 | 5/2007 | Michelson |
| 7,211,086 | B2 | 5/2007 | Biedermann et al. |
| 7,211,087 | B2 | 5/2007 | Young |
| 7,214,227 | B2 | 5/2007 | Colleran et al. |
| 7,223,268 | B2 | 5/2007 | Biedermann |
| 7,229,441 | B2 | 6/2007 | Trieu et al. |

| | | | | | | |
|---|---|---|---|---|---|---|
| 7,264,621 B2 | 9/2007 | Coates et al. | | 2004/0133207 A1 | 7/2004 | Abdou |
| 7,270,665 B2 | 9/2007 | Morrison et al. | | 2004/0138662 A1 | 7/2004 | Landry et al. |
| 7,282,064 B2 | 10/2007 | Chin | | 2004/0143265 A1 | 7/2004 | Landry et al. |
| 7,291,151 B2 | 11/2007 | Alvarez | | 2004/0147928 A1 | 7/2004 | Landry et al. |
| 7,291,153 B2 | 11/2007 | Glascott | | 2004/0147929 A1 | 7/2004 | Biedermann et al. |
| 7,294,128 B2 | 11/2007 | Alleyne et al. | | 2004/0158247 A1 | 8/2004 | Sitiso et al. |
| 7,294,129 B2 | 11/2007 | Hawkins et al. | | 2004/0162560 A1 | 8/2004 | Raynor et al. |
| 7,306,603 B2 | 12/2007 | Boehm, Jr. et al. | | 2004/0172022 A1 | 9/2004 | Landry et al. |
| 7,306,604 B2 | 12/2007 | Carli | | 2004/0172025 A1 | 9/2004 | Drewry et al. |
| 7,306,606 B2 | 12/2007 | Sasing | | 2004/0176766 A1 | 9/2004 | Shluzas |
| 7,314,467 B2 | 1/2008 | Howland | | 2004/0186473 A1 | 9/2004 | Cournoyer et al. |
| 7,316,684 B1 | 1/2008 | Baccelli et al. | | 2004/0204713 A1 | 10/2004 | Abdou |
| 7,322,979 B2 | 1/2008 | Crandall et al. | | 2004/0210216 A1 | 10/2004 | Farris et al. |
| 7,329,258 B2 | 2/2008 | Studer | | 2004/0220567 A1 | 11/2004 | Eisermann et al. |
| 7,335,201 B2 | 2/2008 | Doubler et al. | | 2004/0220671 A1 | 11/2004 | Ralph et al. |
| 7,335,202 B2 | 2/2008 | Matthis et al. | | 2004/0225289 A1 | 11/2004 | Biedermann et al. |
| 7,338,490 B2 | 3/2008 | Ogilvie et al. | | 2004/0236327 A1 | 11/2004 | Paul et al. |
| 7,338,491 B2 | 3/2008 | Baker et al. | | 2004/0236328 A1 | 11/2004 | Paul et al. |
| 7,361,196 B2 | 4/2008 | Fallin et al. | | 2004/0236329 A1 | 11/2004 | Panjabi |
| 7,377,921 B2 | 5/2008 | Studer et al. | | 2004/0236330 A1 | 11/2004 | Purcell et al. |
| 7,476,238 B2 | 1/2009 | Panjabi | | 2004/0249380 A1 | 12/2004 | Glascott |
| 7,491,208 B2 | 2/2009 | Pond, Jr. et al. | | 2004/0260283 A1 | 12/2004 | Wu et al. |
| 7,556,639 B2 | 7/2009 | Rothman et al. | | 2004/0267264 A1 | 12/2004 | Konieczynski et al. |
| 7,559,942 B2 | 7/2009 | Paul et al. | | 2005/0004573 A1 | 1/2005 | Abdou |
| 7,563,274 B2 | 7/2009 | Justis et al. | | 2005/0027296 A1 | 2/2005 | Thramann et al. |
| 7,563,283 B2 | 7/2009 | Kwak | | 2005/0033298 A1 | 2/2005 | Hawkes et al. |
| 7,588,589 B2 | 9/2009 | Falahee | | 2005/0038432 A1 | 2/2005 | Shaolian et al. |
| 7,591,839 B2 | 9/2009 | Biedermann | | 2005/0049708 A1 | 3/2005 | Atkinson et al. |
| 7,601,166 B2 | 10/2009 | Biedermann et al. | | 2005/0055026 A1 | 3/2005 | Biedermann et al. |
| 7,604,654 B2 | 10/2009 | Fallin et al. | | 2005/0065514 A1 | 3/2005 | Studer |
| 7,611,518 B2 | 11/2009 | Walder et al. | | 2005/0065515 A1 | 3/2005 | Jahng |
| 7,621,912 B2 | 11/2009 | Harms et al. | | 2005/0065516 A1 | 3/2005 | Jahng |
| 7,621,940 B2 | 11/2009 | Harms et al. | | 2005/0065517 A1 | 3/2005 | Chin |
| 7,625,393 B2 | 12/2009 | Fallin et al. | | 2005/0070899 A1 | 3/2005 | Doubler et al. |
| 7,632,292 B2 | 12/2009 | Sengupta et al. | | 2005/0080415 A1 | 4/2005 | Keyer et al. |
| 7,641,673 B2 | 1/2010 | Le Couedic et al. | | 2005/0085812 A1 | 4/2005 | Sherman |
| 7,651,515 B2 | 1/2010 | Mack et al. | | 2005/0085813 A1 | 4/2005 | Spitler et al. |
| 7,655,026 B2 | 2/2010 | Justis et al. | | 2005/0085815 A1 | 4/2005 | Harms et al. |
| 7,658,739 B2 | 2/2010 | Shluzas | | 2005/0085816 A1 | 4/2005 | Michelson |
| 7,658,752 B2 | 2/2010 | Labrom et al. | | 2005/0096652 A1 | 5/2005 | Burton |
| 7,682,375 B2 | 3/2010 | Ritland | | 2005/0096654 A1 | 5/2005 | Lin |
| 7,695,496 B2 | 4/2010 | Labrom et al. | | 2005/0107788 A1 | 5/2005 | Beaurain et al. |
| 7,695,498 B2 | 4/2010 | Ritland | | 2005/0113927 A1 | 5/2005 | Malek |
| 7,695,514 B2 | 4/2010 | Kwak | | 2005/0124991 A1 | 6/2005 | Jahng |
| 8,226,690 B2 * | 7/2012 | Altarac et al. ............ 606/256 | | 2005/0131404 A1 | 6/2005 | Mazda et al. |
| 2002/0082602 A1 | 6/2002 | Biedermann et al. | | 2005/0131406 A1 | 6/2005 | Reiley et al. |
| 2002/0143341 A1 | 10/2002 | Biedermann et al. | | 2005/0131407 A1 | 6/2005 | Sicvol et al. |
| 2003/0023243 A1 | 1/2003 | Biedermann et al. | | 2005/0131413 A1 | 6/2005 | O'Driscoll et al. |
| 2003/0100896 A1 | 5/2003 | Biedermann et al. | | 2005/0137597 A1 | 6/2005 | Butler et al. |
| 2003/0105460 A1 | 6/2003 | Crandall et al. | | 2005/0143737 A1 | 6/2005 | Pafford et al. |
| 2003/0109880 A1 | 6/2003 | Shirado et al. | | 2005/0143823 A1 | 6/2005 | Boyd et al. |
| 2003/0114852 A1 | 6/2003 | Biedermann et al. | | 2005/0149020 A1 | 7/2005 | Jahng |
| 2003/0125741 A1 | 7/2003 | Biedermann et al. | | 2005/0149023 A1 | 7/2005 | Ritland |
| 2003/0125742 A1 | 7/2003 | Yuan et al. | | 2005/0154389 A1 | 7/2005 | Selover et al. |
| 2003/0149432 A1 | 8/2003 | Frigg et al. | | 2005/0154390 A1 | 7/2005 | Biedermann et al. |
| 2003/0153911 A1 | 8/2003 | Shluzas | | 2005/0154391 A1 | 7/2005 | Doherty et al. |
| 2003/0163133 A1 | 8/2003 | Altarac et al. | | 2005/0159750 A1 | 7/2005 | Doherty |
| 2003/0171749 A1 | 9/2003 | Le Couedic et al. | | 2005/0165396 A1 | 7/2005 | Fortin et al. |
| 2003/0176862 A1 | 9/2003 | Taylor et al. | | 2005/0165400 A1 | 7/2005 | Fernandez |
| 2003/0191470 A1 | 10/2003 | Ritland | | 2005/0171540 A1 | 8/2005 | Lim et al. |
| 2003/0199873 A1 | 10/2003 | Richelsoph | | 2005/0171543 A1 | 8/2005 | Timm et al. |
| 2003/0208203 A1 | 11/2003 | Lim et al. | | 2005/0177157 A1 | 8/2005 | Jahng |
| 2003/0208204 A1 | 11/2003 | Bailey et al. | | 2005/0177163 A1 | 8/2005 | Abdou |
| 2003/0212398 A1 | 11/2003 | Jackson | | 2005/0177164 A1 | 8/2005 | Walters et al. |
| 2003/0216735 A1 | 11/2003 | Altarac et al. | | 2005/0182401 A1 | 8/2005 | Timm et al. |
| 2003/0220642 A1 | 11/2003 | Freudiger | | 2005/0187548 A1 | 8/2005 | Butler et al. |
| 2003/0220643 A1 | 11/2003 | Ferree | | 2005/0187555 A1 | 8/2005 | Biedermann et al. |
| 2003/0225408 A1 | 12/2003 | Nichols et al. | | 2005/0192571 A1 | 9/2005 | Abdelgany |
| 2004/0002708 A1 | 1/2004 | Ritland | | 2005/0192580 A1 | 9/2005 | Dalton |
| 2004/0006342 A1 | 1/2004 | Altarac et al. | | 2005/0203511 A1 | 9/2005 | Wilson-MacDonald et al. |
| 2004/0049189 A1 | 3/2004 | Le Couedic et al. | | 2005/0203513 A1 | 9/2005 | Jahng et al. |
| 2004/0049190 A1 | 3/2004 | Biedermann et al. | | 2005/0203514 A1 | 9/2005 | Jahng et al. |
| 2004/0073215 A1 | 4/2004 | Carli | | 2005/0203516 A1 | 9/2005 | Biedermann et al. |
| 2004/0078082 A1 | 4/2004 | Lange | | 2005/0203517 A1 | 9/2005 | Jahng et al. |
| 2004/0087949 A1 | 5/2004 | Bono et al. | | 2005/0203518 A1 | 9/2005 | Biedermann et al. |
| 2004/0087952 A1 | 5/2004 | Borgstrom et al. | | 2005/0203519 A1 | 9/2005 | Harms et al. |
| 2004/0092934 A1 | 5/2004 | Howland | | 2005/0216001 A1 | 9/2005 | David |
| 2004/0097933 A1 | 5/2004 | Lourdel et al. | | 2005/0216003 A1 | 9/2005 | Biedermann et al. |
| 2004/0116929 A1 | 6/2004 | Barker et al. | | 2005/0228501 A1 | 10/2005 | Miller et al. |

| | | | | | | |
|---|---|---|---|---|---|---|
| 2005/0234450 A1 | 10/2005 | Barker | | 2006/0069390 A1 | 3/2006 | Frigg |
| 2005/0234451 A1 | 10/2005 | Markworth | | 2006/0074419 A1 | 4/2006 | Taylor et al. |
| 2005/0234452 A1 | 10/2005 | Malandain | | 2006/0074488 A1 | 4/2006 | Abdou |
| 2005/0234453 A1 | 10/2005 | Shaolian et al. | | 2006/0079894 A1 | 4/2006 | Colleran et al. |
| 2005/0234454 A1 | 10/2005 | Chin | | 2006/0079895 A1 | 4/2006 | McLeer |
| 2005/0234456 A1 | 10/2005 | Malandain | | 2006/0079896 A1 | 4/2006 | Kwak |
| 2005/0240181 A1 | 10/2005 | Boomer et al. | | 2006/0079898 A1 | 4/2006 | Ainsworth |
| 2005/0240183 A1 | 10/2005 | Vaughan | | 2006/0079899 A1 | 4/2006 | Ritland |
| 2005/0245930 A1 | 11/2005 | Timm et al. | | 2006/0084977 A1 | 4/2006 | Liebermann |
| 2005/0251137 A1 | 11/2005 | Ball | | 2006/0084981 A1 | 4/2006 | Shluzas |
| 2005/0251139 A1 | 11/2005 | Roh | | 2006/0084982 A1 | 4/2006 | Kim |
| 2005/0251140 A1 | 11/2005 | Shaolian et al. | | 2006/0084983 A1 | 4/2006 | Kim |
| 2005/0251141 A1 | 11/2005 | Frigg et al. | | 2006/0084984 A1 | 4/2006 | Kim |
| 2005/0260058 A1 | 11/2005 | Cassagne, III | | 2006/0084985 A1 | 4/2006 | Kim |
| 2005/0261685 A1 | 11/2005 | Fortin et al. | | 2006/0084987 A1 | 4/2006 | Kim |
| 2005/0261687 A1 | 11/2005 | Garamszegi et al. | | 2006/0084988 A1 | 4/2006 | Kim |
| 2005/0267470 A1 | 12/2005 | McBride | | 2006/0084989 A1 | 4/2006 | Dickinson et al. |
| 2005/0267471 A1 | 12/2005 | Biedermann et al. | | 2006/0084991 A1 | 4/2006 | Borgstrom |
| 2005/0267474 A1 | 12/2005 | Dalton | | 2006/0084993 A1 | 4/2006 | Landry et al. |
| 2005/0267477 A1 | 12/2005 | Jackson | | 2006/0084995 A1 | 4/2006 | Biedermann et al. |
| 2005/0273099 A1 | 12/2005 | Baccelli et al. | | 2006/0085069 A1 | 4/2006 | Kim |
| 2005/0273101 A1 | 12/2005 | Schumacher | | 2006/0089643 A1 | 4/2006 | Mujwid |
| 2005/0273120 A1 | 12/2005 | Abdou | | 2006/0089644 A1 | 4/2006 | Felix |
| 2005/0277919 A1 | 12/2005 | Slivka et al. | | 2006/0095037 A1 | 5/2006 | Jones et al. |
| 2005/0277922 A1 | 12/2005 | Trieu et al. | | 2006/0106380 A1 | 5/2006 | Colleran et al. |
| 2005/0277923 A1 | 12/2005 | Sweeney | | 2006/0106381 A1 | 5/2006 | Ferree |
| 2005/0277925 A1 | 12/2005 | Mujwid | | 2006/0106383 A1 | 5/2006 | Biedermann et al. |
| 2005/0277927 A1 | 12/2005 | Guenther et al. | | 2006/0111714 A1 | 5/2006 | Foley |
| 2005/0277928 A1 | 12/2005 | Boschert | | 2006/0111715 A1 | 5/2006 | Jackson |
| 2005/0277931 A1 | 12/2005 | Sweeney et al. | | 2006/0116677 A1 | 6/2006 | Burd et al. |
| 2005/0277934 A1 | 12/2005 | Vardiman | | 2006/0122597 A1 | 6/2006 | Jojnes et al. |
| 2005/0283152 A1 | 12/2005 | Lindemann et al. | | 2006/0122599 A1 | 6/2006 | Drewry |
| 2005/0283157 A1 | 12/2005 | Coates et al. | | 2006/0129147 A1 | 6/2006 | Biedermann et al. |
| 2005/0283238 A1 | 12/2005 | Reiley | | 2006/0129149 A1 | 6/2006 | Iott et al. |
| 2005/0283244 A1 | 12/2005 | Gordon et al. | | 2006/0129239 A1 | 6/2006 | Kwak |
| 2005/0288669 A1 | 12/2005 | Abdou | | 2006/0142758 A1 | 6/2006 | Petit |
| 2005/0288670 A1 | 12/2005 | Panjabi | | 2006/0142760 A1 | 6/2006 | McDonnell |
| 2005/0288671 A1 | 12/2005 | Yuan et al. | | 2006/0142761 A1 | 6/2006 | Landry et al. |
| 2005/0288672 A1 | 12/2005 | Ferree | | 2006/0149228 A1 | 7/2006 | Schlapfer |
| 2005/0288673 A1 | 12/2005 | Catbagan et al. | | 2006/0149229 A1 | 7/2006 | Kwak |
| 2006/0004357 A1 | 1/2006 | Lee et al. | | 2006/0149232 A1 | 7/2006 | Sasing |
| 2006/0004359 A1 | 1/2006 | Kramer et al. | | 2006/0149238 A1 | 7/2006 | Sherman et al. |
| 2006/0004360 A1 | 1/2006 | Kramer et al. | | 2006/0149241 A1 | 7/2006 | Richelsoph et al. |
| 2006/0004363 A1 | 1/2006 | Brockmeyer et al. | | 2006/0149244 A1 | 7/2006 | Amrein et al. |
| 2006/0009767 A1 | 1/2006 | Kiester | | 2006/0149278 A1 | 7/2006 | Abdou |
| 2006/0009768 A1 | 1/2006 | Ritland | | 2006/0155277 A1 | 7/2006 | Metz-Stavenhagen |
| 2006/0009769 A1 | 1/2006 | Liebermann | | 2006/0155278 A1 | 7/2006 | Warnick |
| 2006/0009770 A1 | 1/2006 | Speirs et al. | | 2006/0161152 A1 | 7/2006 | Ensign et al. |
| 2006/0009775 A1 | 1/2006 | Dec et al. | | 2006/0161154 A1 | 7/2006 | McAfee |
| 2006/0009780 A1 | 1/2006 | Foley et al. | | 2006/0167454 A1 | 7/2006 | Ludwig et al. |
| 2006/0009846 A1 | 1/2006 | Trieu et al. | | 2006/0167455 A1 | 7/2006 | Clement et al. |
| 2006/0015099 A1 | 1/2006 | Cannon et al. | | 2006/0173454 A1 | 8/2006 | Spitler et al. |
| 2006/0015104 A1 | 1/2006 | Dalton | | 2006/0173456 A1 | 8/2006 | Hawkes et al. |
| 2006/0025767 A1 | 2/2006 | Khalili | | 2006/0184171 A1 | 8/2006 | Biedermann |
| 2006/0025768 A1 | 2/2006 | Iott et al. | | 2006/0184180 A1 | 8/2006 | Augostino |
| 2006/0025770 A1 | 2/2006 | Schlapfer et al. | | 2006/0189983 A1 | 8/2006 | Fallin |
| 2006/0030850 A1 | 2/2006 | Keegan et al. | | 2006/0189984 A1 | 8/2006 | Fallin |
| 2006/0036240 A1* | 2/2006 | Colleran et al. ............ 606/61 | | 2006/0189985 A1 | 8/2006 | Lewis |
| 2006/0036242 A1 | 2/2006 | Nilsson et al. | | 2006/0195090 A1 | 8/2006 | Suddaby |
| 2006/0036244 A1 | 2/2006 | Spitler et al. | | 2006/0195093 A1 | 8/2006 | Jahng |
| 2006/0036246 A1 | 2/2006 | Carl et al. | | 2006/0195098 A1 | 8/2006 | Schumacher |
| 2006/0036252 A1 | 2/2006 | Baynham et al. | | 2006/0200128 A1 | 9/2006 | Mueller |
| 2006/0036254 A1 | 2/2006 | Lim | | 2006/0200130 A1 | 9/2006 | Hawkins |
| 2006/0036256 A1 | 2/2006 | Carl et al. | | 2006/0200131 A1 | 9/2006 | Chao et al. |
| 2006/0036259 A1 | 2/2006 | Carl et al. | | 2006/0200132 A1 | 9/2006 | Chao et al. |
| 2006/0036260 A1 | 2/2006 | Runco et al. | | 2006/0200135 A1 | 9/2006 | Sherman et al. |
| 2006/0036323 A1 | 2/2006 | Carl et al. | | 2006/0200138 A1 | 9/2006 | Michelson |
| 2006/0036324 A1 | 2/2006 | Sachs et al. | | 2006/0200139 A1 | 9/2006 | Michelson |
| 2006/0041259 A1 | 2/2006 | Paul et al. | | 2006/0200149 A1 | 9/2006 | Hoy et al. |
| 2006/0052780 A1 | 3/2006 | Errico et al. | | 2006/0210494 A1 | 9/2006 | Rabiei et al. |
| 2006/0052783 A1 | 3/2006 | Dant et al. | | 2006/0212033 A1 | 9/2006 | Rothman |
| 2006/0052784 A1 | 3/2006 | Dant et al. | | 2006/0212034 A1 | 9/2006 | Triplett et al. |
| 2006/0052786 A1 | 3/2006 | Dant et al. | | 2006/0217710 A1 | 9/2006 | Abdou |
| 2006/0052872 A1 | 3/2006 | Studer et al. | | 2006/0217713 A1 | 9/2006 | Serhan et al. |
| 2006/0058788 A1 | 3/2006 | Hammer et al. | | 2006/0217714 A1 | 9/2006 | Serhan et al. |
| 2006/0058790 A1 | 3/2006 | Carl et al. | | 2006/0217716 A1 | 9/2006 | Baker et al. |
| 2006/0064090 A1 | 3/2006 | Park | | 2006/0217719 A1 | 9/2006 | Albert et al. |
| 2006/0064091 A1 | 3/2006 | Ludwig et al. | | 2006/0229608 A1 | 10/2006 | Foster |
| 2006/0064092 A1 | 3/2006 | Howland | | 2006/0229609 A1 | 10/2006 | Wang |

| | | |
|---|---|---|
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmannt |
| 2006/0264942 A1 | 11/2006 | Lim et al. |
| 2006/0264962 A1 | 11/2006 | Chin et al. |
| 2006/0269940 A1 | 11/2006 | Li et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282078 A1 | 12/2006 | Labrom |
| 2006/0282079 A1 | 12/2006 | Labrom |
| 2007/0093828 A1 | 4/2007 | Abdou |
| 2007/0093829 A1 | 4/2007 | Abdou |
| 2007/0106383 A1 | 5/2007 | Abdou |
| 2007/0123884 A1 | 5/2007 | Abdou |

FOREIGN PATENT DOCUMENTS

| | | |
|---|---|---|
| WO | WO 2004/084774 | 10/2004 |
| WO | WO 2004/093702 | 11/2004 |
| WO | WO 2005/122922 | 12/2005 |
| WO | WO 2006/041963 | 4/2006 |
| WO | WO 2006/058221 | 6/2006 |
| WO | WO 2006/089292 | 8/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |

* cited by examiner

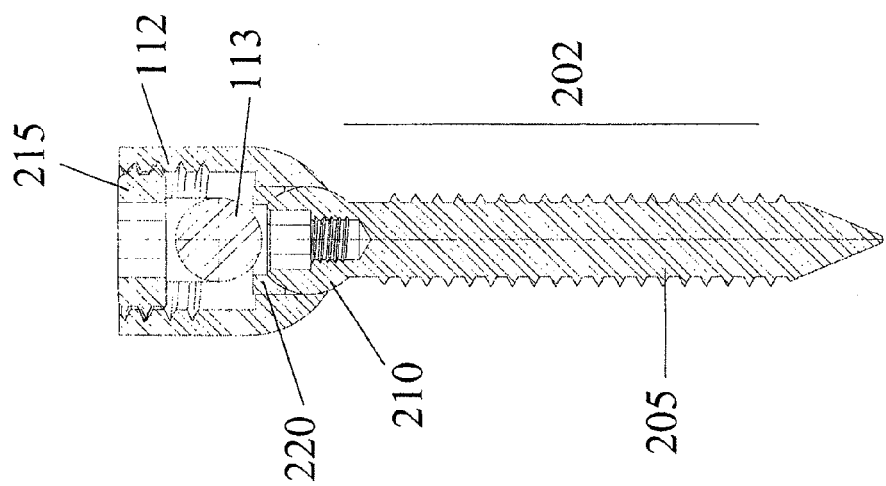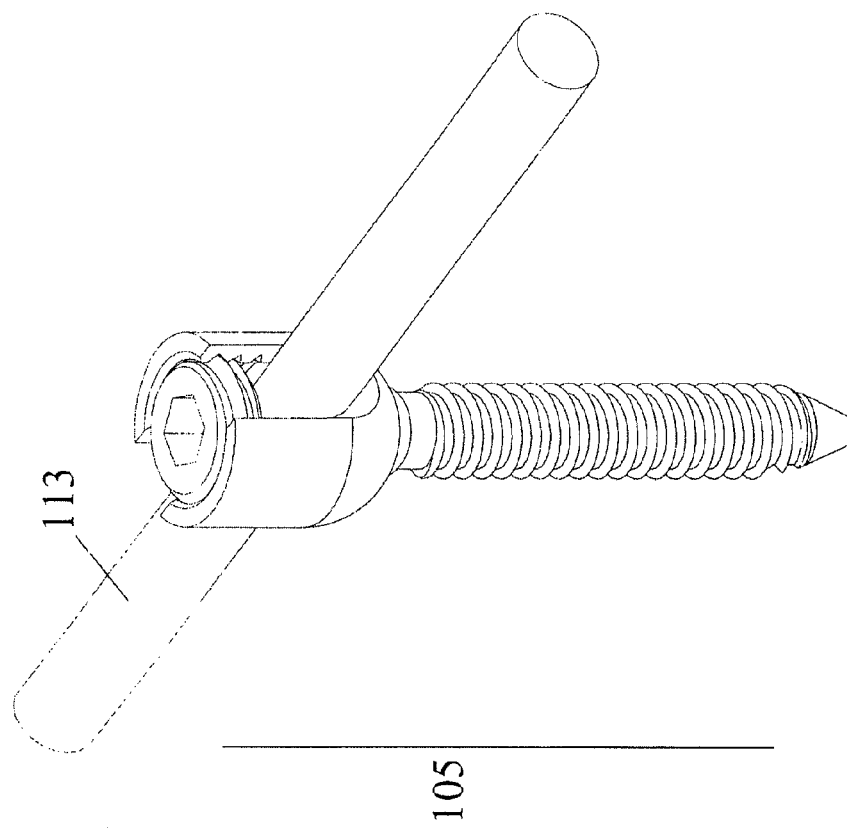

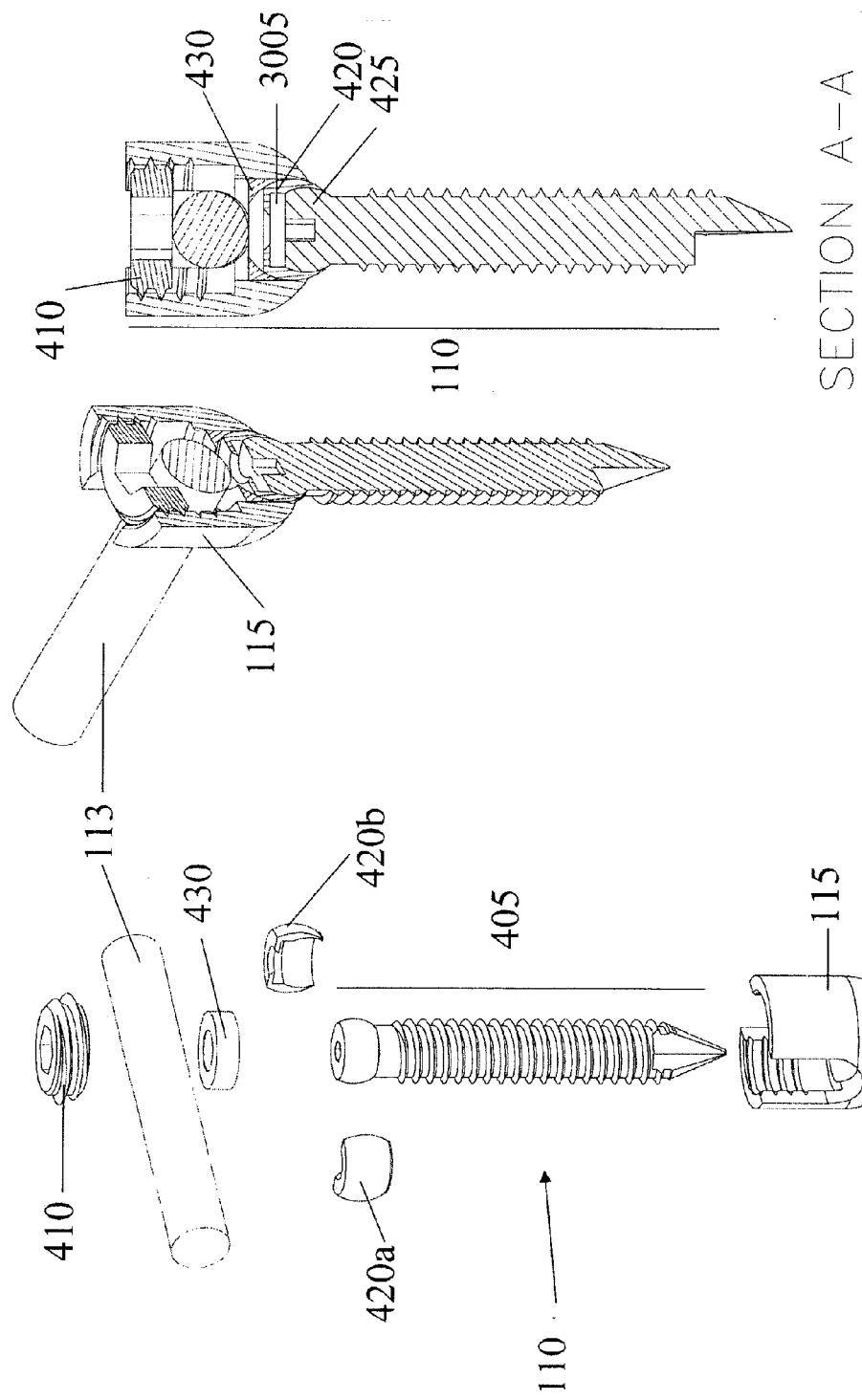

DEVICES AND METHODS FOR INTER-VERTEBRAL ORTHOPEDIC DEVICE PLACEMENT

REFERENCE TO PRIORITY DOCUMENT

This application is a continuation of U.S. patent application Ser. No. 11/613,074, entitled "Devices and Methods for Inter-vertebral Orthopedic Device Placement," filed Dec. 19, 2006 now U.S. Pat. No. 7,704,271, which claims priority of co-pending U.S. Provisional Patent Application Ser. No. 60/751,772, filed Dec. 19, 2005. Priority of the aforementioned filing dates is hereby claimed and the disclosures of the Applications are hereby incorporated by reference in their entirety.

BACKGROUND

The disclosure relates to devices and methods for stabilization of the bony elements of the skeleton. The method and the devices permit adjustment and maintenance of the spatial relationship(s) between neighboring bones. Depending on the specifics of the design, the motion between skeletal segments may be increased, reduced, returned to the normal physiology state or modulated in any desired manner.

Spinal disease is a major health problem in the industrialized world and the surgical treatment of spinal pathology is an evolving discipline. Alteration in the anatomical alignment and physiologic motion that normally exists between adjacent spinal vertebrae can cause significant pain, weakness, deformity and disability. The traditional surgical treatment of abnormal vertebral motion has been the complete immobilization and bony fusion of the involved spinal segments. An extensive array of surgical techniques and implantable devices has been formulated to accomplish this goal.

The growing experience with spinal fusion has shed light on the long-term consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The second procedure necessitates re-dissection through the prior, scarred operative field and carries significantly greater risk than the initial procedure while providing a reduced probability of pain relief. Further, extension of the fusion will increase the load on the motion segments that now lie at either end of the fusion construct and will accelerate the rate of degeneration at those levels. Thus, spinal fusion begets additional fusion surgery.

In view of the proceeding, there is a growing recognition that segmental spinal fusion and complete immobilization is an inadequate solution to abnormal spinal motion and vertebral mal-alignment. Correction of the abnormal movement and preservation of spinal mobility is a more intuitive and rational treatment option. It is appropriate to employ motion correction in the initial treatment plan and reserve complete immobilization and fusion for those patients with advanced motion abnormalities that can not be corrected.

Currently, a variety of spinal motion patterns are considered indications of advanced spinal instability. Patients with these motions patterns who develop pain are considered ineligible for treatment strategies that preserve spinal mobility. In particular, aberrant motion at levels of vertebral mal-alignment is considered an indication of disease that can not be corrected with current motion preservation methods. That is, surgeons believe that current motion correction techniques have a limited capacity to support the diseased spinal segments and those spinal segments with vertebral mal-aligned are too unstable to be effectively treated by these techniques. Fusion and complete segmental immobilization remains the main surgical option for the surgical treatment of these patients.

The current limitations of motion preservation techniques needlessly relegate a large number of patients to fusion surgery and the numerous disadvantages of complete spinal immobilization. A method for the treatment of segments with aberrant motion and/or spinal mal-alignment without fusion is clearly needed. It would correct the abnormal motion and preserve mobility in a significant number of patients who must currently undergo spinal fusion.

SUMMARY

Spinal segments with abnormal motion and/or spinal mal-alignment can be successfully treated with devices that preserve mobility. Within a given spinal segment, the stable vertebral level is identified. Within the lower lumbar spine, that level is most commonly at the sacrum. A bone fastener is rigidly affixed to the stable spinal segment and an interconnecting member is rigidly affixed to the bone fastener so as to form a cantilever construct. Vertebral bodies that exhibit aberrant spinal motion and/or mal-alignment relative to the stable segment are then attached to the interconnecting member using non-rigid bone fastener(s). The motion profile of the dynamic fastener can be varied and may be selected to provide the desired vertebral motion characteristics.

The interconnecting member may be rigid or it may be alternatively made rigid parallel to the direction of greatest instability and non-rigid in the other planes. The latter embodiments provide additional degrees of freedom and motion characteristics.

In one aspect, there is disclosed a method of vertebral stabilization, comprising: rigidly affixing a first bone fastener to a first vertebral body and to an interconnecting member such that the interconnecting member is rigidly cantilevered from the first vertebral body; and affixing a second vertebral body to the interconnecting member such that the second vertebral body is attached to the interconnecting member in a manner that permits at least some movement between the second vertebral body and the first vertebral body.

In another aspect, there is disclosed a method of vertebral stabilization, comprising: rigidly affixing a first vertebral body to at least a portion of an interconnecting member such that the first vertebral body and the portion of the interconnecting member collectively form a rigid base; and affixing a second vertebral body to the rigid base in a manner that permits relative movement between the second vertebral body and the first vertebral body.

In another aspect, there is disclosed a method of vertebral stabilization, comprising: rigidly attaching an interconnecting member to a first vertebral body such that the interconnecting member is rigidly cantilevered relative to the first vertebral body; and attaching a second vertebral body to the interconnecting member such that the second vertebral body can move relative to the first vertebral body.

Other features and advantages will be apparent from the following description of various devices and methods, which illustrate, by way of example, the principles of these embodiments.

BRIEF DESCRIPTION OF THE DRAWINGS

FIGS. 4A and 4B show perspective and cross-sectional views of an exemplary embodiment of a bone screw assembly that rigidly attaches to a rod.

FIG. 5A shows an exploded view of an exemplary embodiment of a dynamic bone fastener or screw assembly.

FIG. 5B shows cross-sectional views of the dynamic bone screw assembly.

DETAILED DESCRIPTION

Disclosed are devices and methods for providing segmental stabilization of bone segments while still preserving at least some relative motion between the segments. In an embodiment, one or more bone fasteners are rigidly attached to a bone segment at a stable level. An interconnecting member is then rigidly attached to the bone fastener(s) such that the interconnecting member extends outwardly from the fastener(s) and forms a cantilever construct. The bone fastener(s) and cantilevered interconnecting member provide a rigid, stable base to which adjacent bone segments can be movably attached. The adjacent bone segments are attached to the interconnecting member using a dynamic bone fastener(s) that is attached to the adjacent segment. The dynamic bone fastener permits at least some movement and, in this way, the adjacent segments can be dynamically attached to the stable vertebral segment.

The devices and methods are described herein in the context of bone segments comprised of the sacrum and the two lowermost lumbar vertebrae. Within the lumbar spine, these vertebral segments are the ones most commonly affected by degenerative disease and most often afflicted with abnormal alignment and pathologic motion. It should be appreciated that the devices and methods described herein are not limited to use within the lumbar spine and that they are equally suited for use with other skeletal segments.

Figure 2:
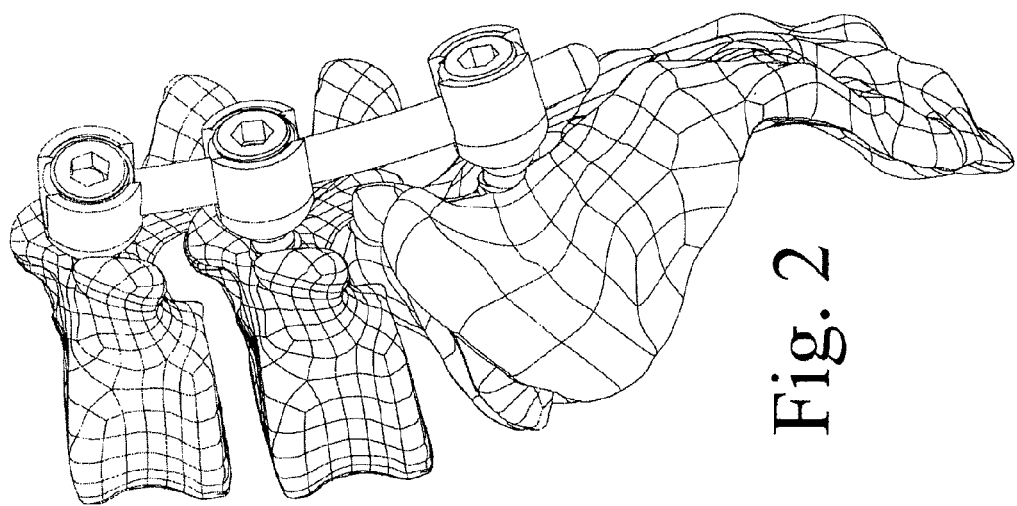
FIGS. 1 and 2 show perspective views of the sacrum and the two lower most lumbar vertebrae.
Figure 1:
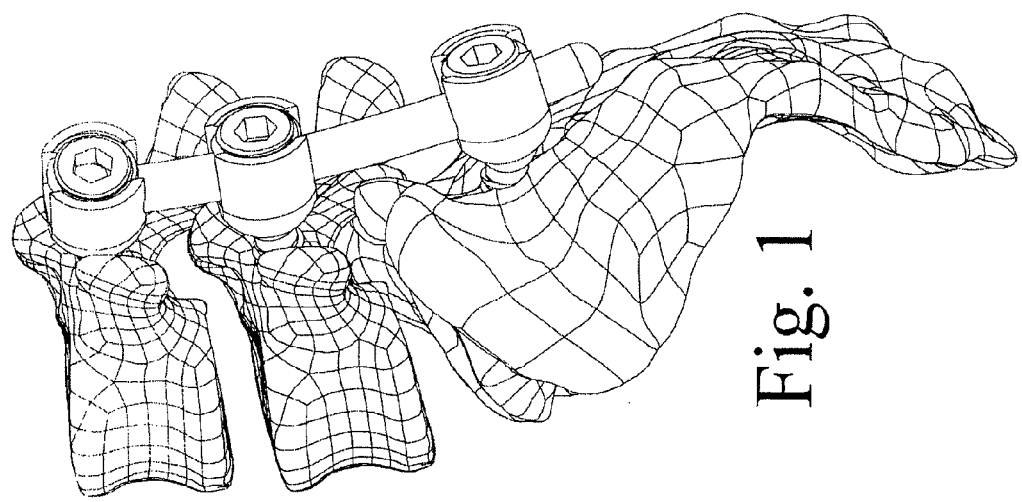
Figure 3:
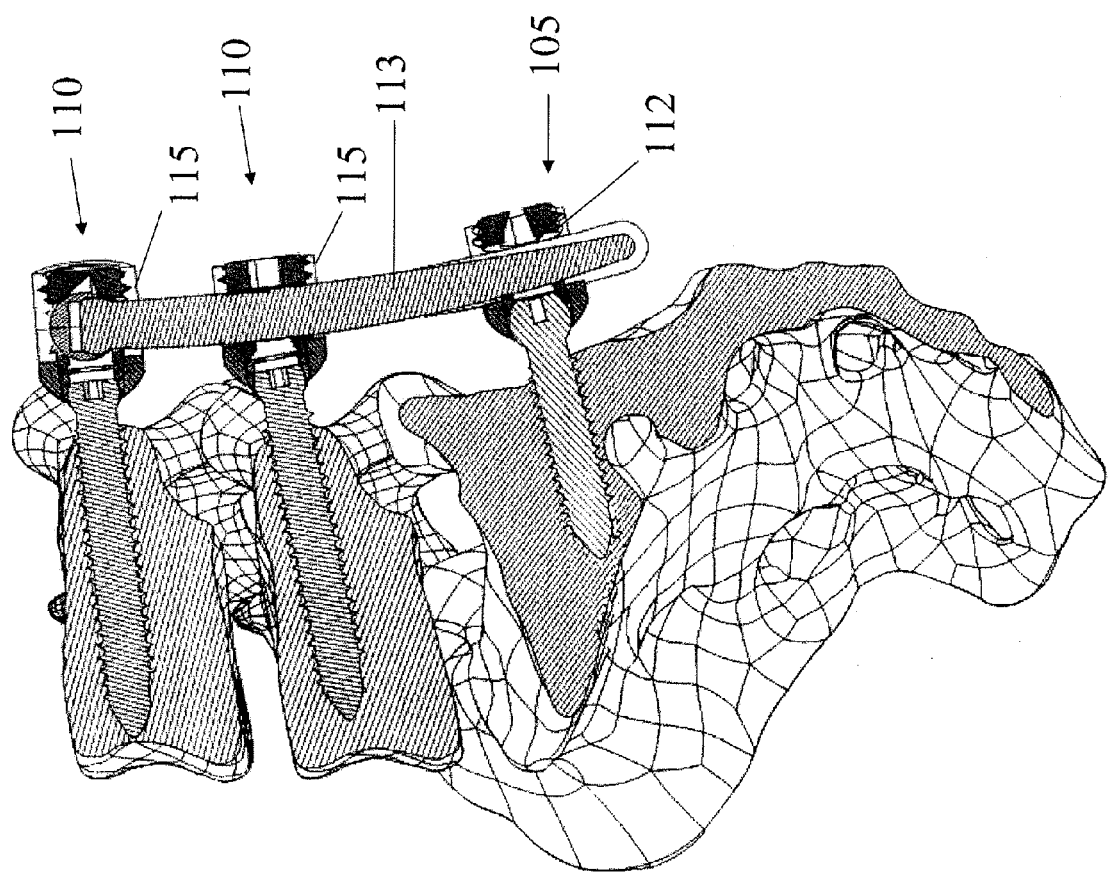
FIG. 3 shows a cross sectional view of the sacrum and the two lower most lumbar vertebrae wherein the plane of section is along the long axis of the bone screws.

FIG. 1 shows a perspective view of the sacrum and the two lowermost lumbar vertebrae while FIG. 2 shows a schematic representation of the same view. In FIG. 3, a cross sectional illustration is shown wherein the plane of section is along the long axis of the bone screws. A bone screw assembly 105 is inserted into the sacrum such that a shank portion of a bone screw is rigidly positioned inside the sacrum. The bone screw assembly 105 includes a receiver 112 that rigidly attaches to a rod 113, as described in more detail below. The rod 113 extends outwardly from the bone screw assembly in cantilever fashion. In an embodiment, the bone screw assembly 105 is rigidly attached to the sacrum such that there is no movement between the bone screw assembly and the sacrum. In addition, the bone screw assembly 105 is rigidly attached to the rod 113 such that there is no movement between the bone screw assembly 105 and the rod 113. Thus, the rod 113 is immobilized relative to the sacrum. In this manner, the sacrum, bone screw assembly, and rod collectively form a rigid and stable base to which one or more additional bone segments can be attached.

With reference still to FIG. 3, bone screw assemblies 110 are inserted into each of the two lower most lumbar vertebrae such that shank portions of the screws are rigidly positioned inside the vertebrae such as within the pedicle segment of bone. Each of the bone screws assemblies 110 includes a receiver 115 that attaches to the rod 113 in a manner that permits at least some movement between the receiver 115 and the rod 113, as described in more detail below. In an embodiment, a screw of the assembly 115 rigidly attaches to the respective vertebrae, while a head of the screw is movably housed within a member 420 that is rigidly affixed to receiver 115. A bearing surface exists between the inner aspect of member 420 and the head of the bone screw. Thus, the vertebrae are movably attached to the rod via the bone screw assemblies 110. In this manner, the vertebrae are stabilized relative to the stable base (the rigid framework of the sacrum, bone screw assembly 105, and rod 113) while still permitting at least some motion relative to the stable base. In other words, the rigid screw assembly 105 and rod 113 form a cantilever framework that is attached to the stable segment (sacrum). The dynamic screw assemblies 110 are then anchored into the vertebral bodies with abnormal alignment and/or motion and attached to the rigid rod. FIGS. 1, 2 and 3 show bone screw assemblies attached to a single side of the vertebral midline (unilateral placement) although it should be appreciated that screw insertion is preferably performed on both sides of the midline in actual practice. Further, while the illustrated embodiment shows a single bone screw assembly attached to each side of a vertebral body, more than one screw assembly may be used. Multiple screw attachment is particularly useful at the sacrum where the cantilevered interconnecting member may be affixed to the sacrum at multiple points. Multiple methods of sacral fixation are well known in the art and any of these may be utilized.

FIGS. 4A and 4B show perspective and cross-sectional views of an exemplary embodiment of the bone screw assembly that rigidly attaches to the rod 113. The bone screw assembly 105 includes a screw 202 with a shank 205 attached to a head 210. The head 210 sits within a seat in the rod receiver 112. A locking nut 215 can be tightened or advanced into the receiver 112 to compress the rod 113 onto the head 210 via a member 220 positioned between the head 210 and rod 113. When locking nut 215 is advanced, it forces the rod 113 against the member 220 which, in turn, compresses the screw head 210 against the inner aspect of receiver 112. When the locking nut 112 is fully advanced, the entire assembly becomes rigid and immobilizes the bone screw 202 relative to the receiver 112 and the rod 113.

It should be appreciated that the embodiment of the rigid bone screw shown in FIGS. 4A and 4B is exemplary and that other types of assemblies for rigidly attaching a bone screw to a rod can be used.

FIG. 5A shows an exploded view of the dynamic bone screw assembly 110 while FIG. 5B shows cross-sectional views of the screw assembly. As mentioned, the bone screw assembly 110 is dynamic in that it permits relative movement between the bone screw and the receiver 115. When the assembly is locked by the advancement of locking nut 410, the inner housing member 420 is immobilized relative to the receiver 115 and the contained rod 113 while the bone screw is rigidly attached to the vertebral body. However, the head of the screw can move in a ball and socket manner rotate within the inner housing member so as to permit continued movement between the bone screw and the interconnecting rod 113.

With reference to FIGS. 5A and 5B, the bone screw assembly 110 includes a receiver 115 and a bone screw 405, which couple to the rod 113. A locking nut 410 can be threaded into the receiver 115 to provide a downward force onto the rod 113 and immobilize the rod relative to the receiver 115 and the inner housing (420a and 420b). The bone screw 405 has a head 425 that can be positioned within inner housing members 420a and 420b. While not shown, half members 420a and 420b are joined to form the assembled inner housing member using threaded screws, ratchets, clips, adhesives, or any other well-known technique for segment assembly. A saddle 430 is positioned within the receiver 115 below the rod 113 and above the inner housing members 420 in the assembled device.

As shown in FIG. 5B, the head 425 of the screw 405 is positioned within the inner housing members 420, which collectively form a socket for the spherical head 425. The inner aspect of inner housing member 420 contains space 3005 that is positioned above the head 425. The saddle 430 is positioned directly above the inner housing 420 assembly and below the rod 113. In use, screw 405 is advanced into the underlying bone and affixed to it. Rod receiver 115 is freely movable relative to screw 115 based on the movement between the outer aspect of the inner housing member 420 and the complimentary spherical cut-out within the inner aspect of receiver 115. Rod 113 is positioned within the movable receiver 115 and the locking nut 410 is advanced toward the rod 113 to tightly press the rod 113 against the upper edge of the saddle 430. This causes the saddle 430 to press downward against the inner housing members 420 and forcefully seat it within receiver 115. In this way, rod 113, saddle 430, inner housing members 420 and receiver 115 are rigidly immobilized relative to one another. However, the head 425 of the bone screw 405 remains movable within the inner aspect of the inner housing members 420 to produces the dynamic properties of the assembly.

The space 3005 within the inner housing member 420 preferably contains a material or structure that resists movement of the head 425 of the bone screw 405 relative to the inner aspect of the inner housing members 420. Belleville washer(s), compression springs and the like can be placed within space 3005 to resist screw head movement and keep the upper surface of the screw head and upper surface of space 3005 in a parallel configuration. Alternatively, the material or structure within the space 3005 can be, for example, an elastic material(s), fluids, spring device(s), magnets or any other appropriate materials/devices that will resist movement of the head of bone screw relative to the inner aspect of the inner housing members. Clearly, the motion profile of the whole screw assembly will depend on the resistance characteristics of the material/device placed within space 3005. In this way, the motion of the dynamic fastener can be varied by changing the material in space 3005 and the fastener may be selected to provide the desired vertebral motion characteristics.

When the screw head is moved out of a predetermined neutral position within the inner housing members, the material/device in space 3005 will apply a force to the head of screw and resist any movement away from the neutral position. The assembly will return the screw and the attached bone to the neutral position once the deflecting force has dissipated. Further, since movement in the pre-locked configuration of the screw assembly occurs between the outer aspect of the inner housing 420 and receiver 115, the surgeon can freely adjust the orientation of the receiver 115 relative to the bone screw 405 before locking the assembly without influencing the assembly's neutral position or pre-loading the bone/screw interface.

It should be appreciated that the embodiment of the dynamic bone screw shown in FIGS. 5A and 5B is exemplary and that other types of assemblies for movably attaching a bone screw to a rod can be used.

Figure 6A:
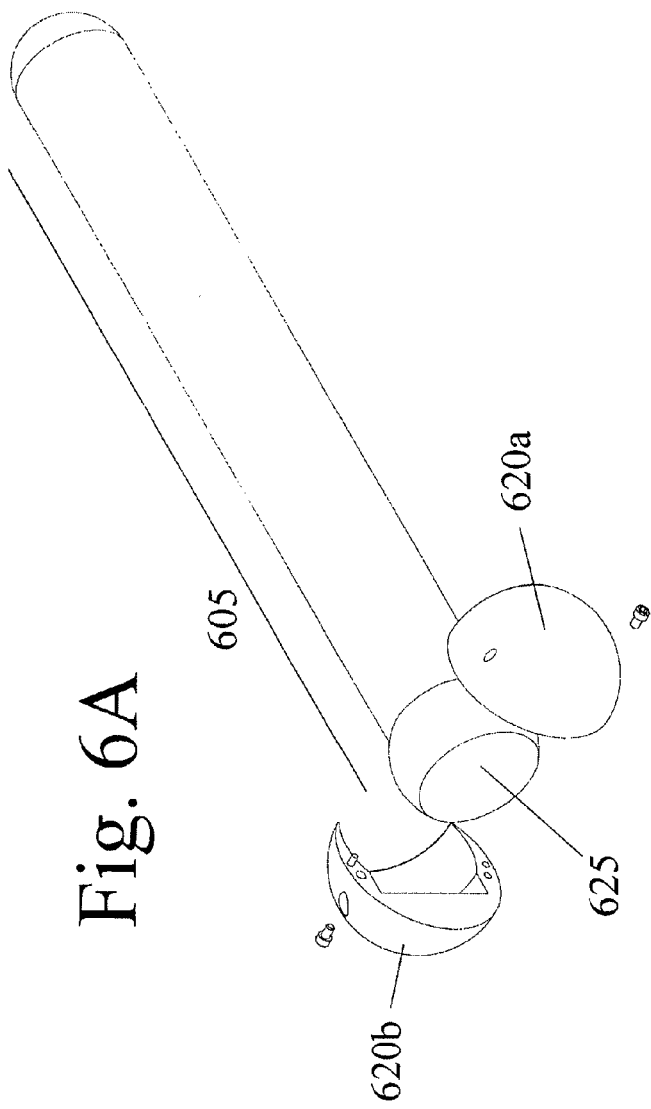
FIGS. 6A and 6B show a perspective exploded view and cross-sectional view of a dynamic rod device.
Figure 6B:
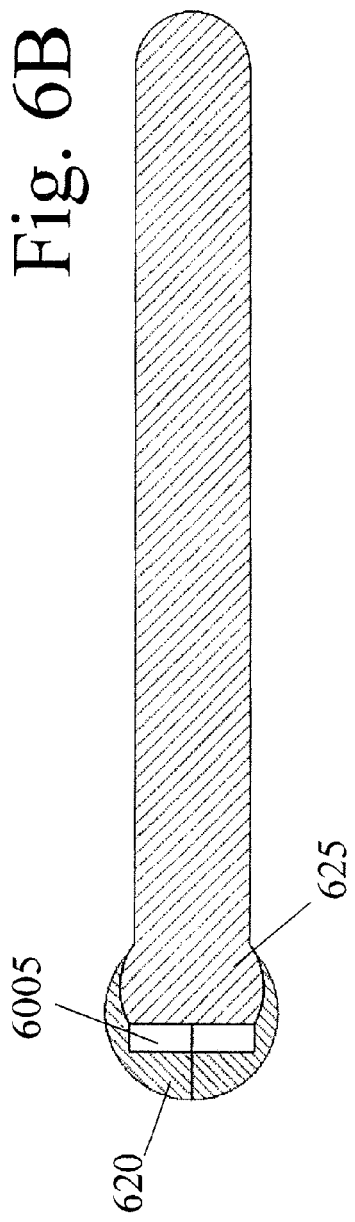
Figure 7A:
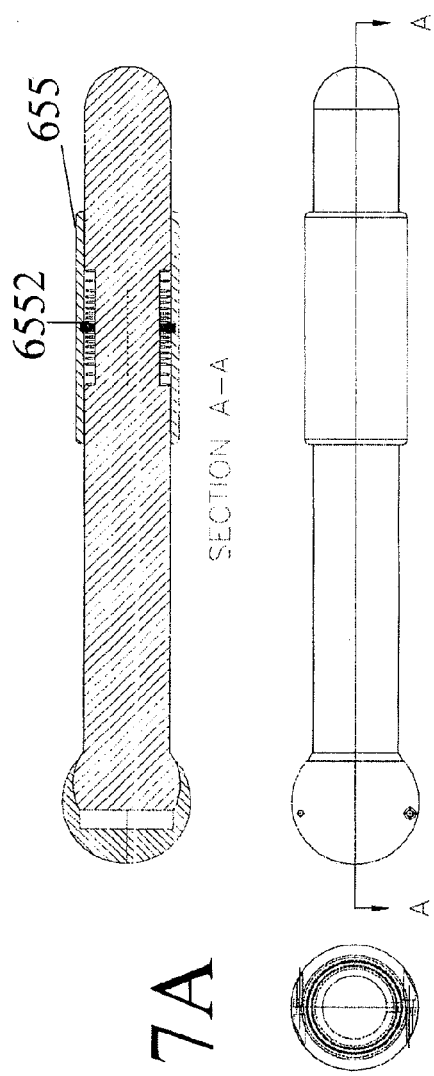
FIG. 7A shows the dynamic rod device equipped with a dynamic sleeve
Figure 7B:
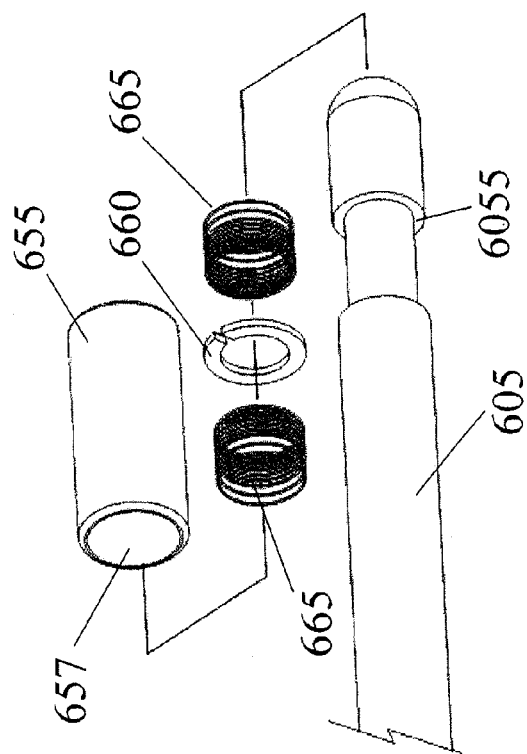
FIG. 7B shows an exploded view of one end of the dynamic rod device.

The interconnecting member may be of any applicable configuration and/or design. Commonly, the interconnecting member is rod-based, plate-based, loop-based or a combination of these elements. With reference to FIG. 3, the interconnecting member is a rod. The rod may be rigid or it may have dynamic features that confer additional motion characteristics onto to the assembled construct. The rod illustrated in FIG. 3 contains a dynamic terminus. FIGS. 6A and 6B show a perspective exploded view and cross-sectional view of the dynamic rod device, respectively. The dynamic feature is similar in design to the dynamic screw assembly 110 that is shown in FIG. 5. That is, the rod 605 has a head 625 that can be positioned within inner housing members 620a and 620b. Partial members 620a and 620b are joined to form the assembled inner housing member using threaded screws, but ratchets, clips, adhesives, or any other well-known technique for segment assembly may be alternatively used. The inner aspect of inner housing member 620 contains a space 6005 that is positioned above the head 625. The space 6005 within the inner housing member 620 preferably contains a material or structure that resists movement of the head 625 of the rod relative to the inner aspect of the inner housing members 620. With movement of head 625 away from the predetermined neutral position within the inner housing members 620, the material/device in space 6005 will apply a force to head 625 and resist any movement away from the neutral position. FIG. 7A shows a dynamic sleeve that has been added to the embodiment of FIG. 6 while FIG. 7B shows an exploded view of one end of the rod. Outer sleeve 655 has internal bore 657 that receives rod 605. Indentation 6552 is located on the inner wall of bore 657 and is configured to accept ring 660. Rod 605 has recess 6055. In assembly, each spring 665 is placed on either side of ring 660. The ring is retained within indentation 6552 of sleeve 655 and functions to limit the extent of travel and retain the device in assembled configuration.

Figure 8A:
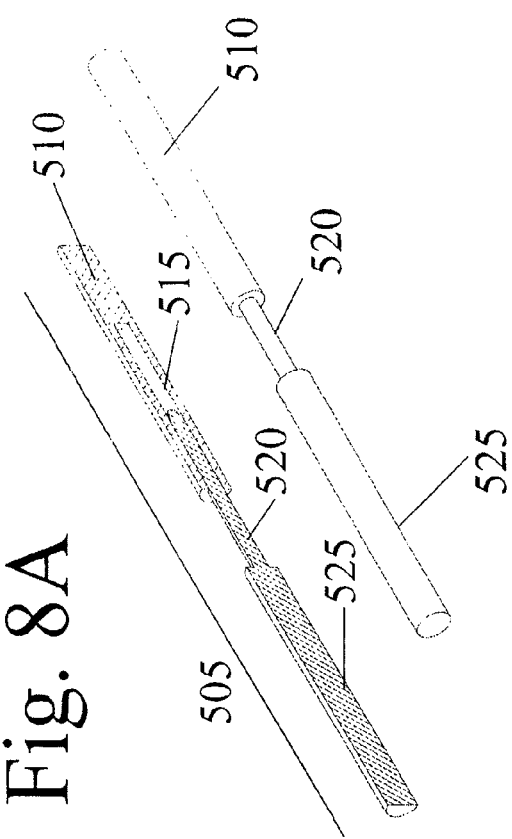
FIGS. 8A and 8B show embodiments of a rod that is adapted to provide movement along the long axis of the rod.
Figure 8B:
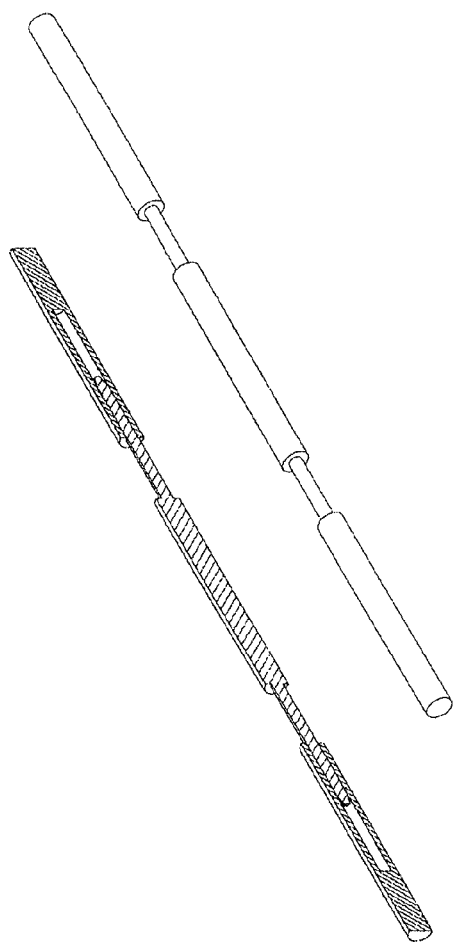

Another embodiment of a dynamic feature is shown in FIGS. 8A and 8B. The rod is adapted to permit movement in the direction of the long axis (even If the axis is curvilinear). In FIG. 8A, the rod 505 includes a first rod segment 510 having an internal bore 515 that slidably receives a shaft portion 520 of a second rod segment 525 wherein the first rod segment 510 and second rod segment 525 are movable relative to one another. In FIG. 8B, the rod 505 can include more than two segments.

Figure 9A:
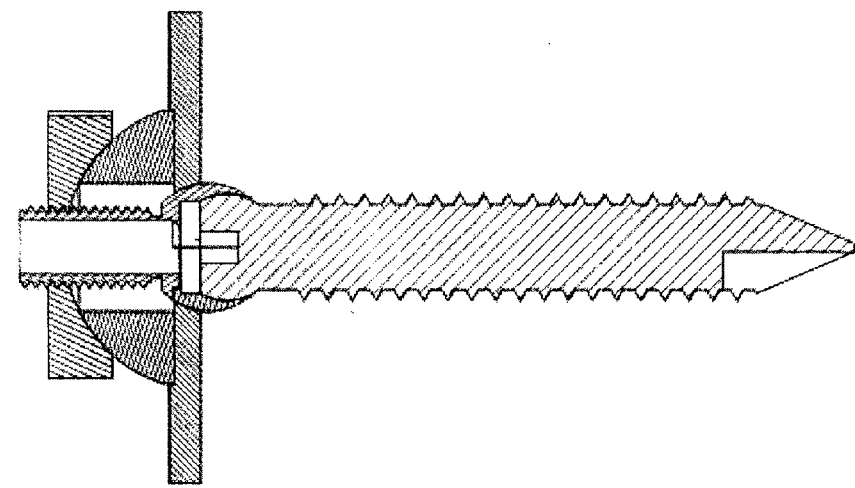
FIGS. 9A and 9B show an alternative dynamic screw assembly that may be used with a plate-based inter-connecting member.
Figure 9B:
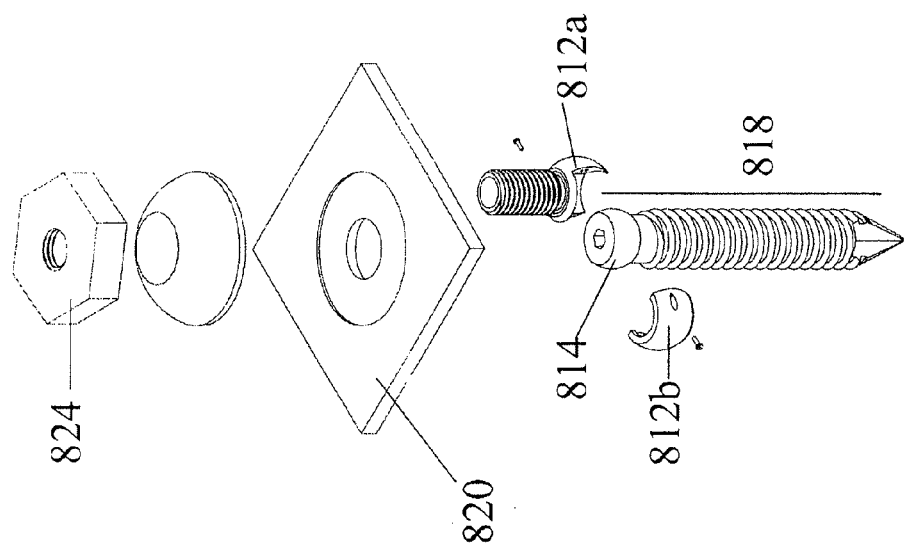

FIGS. 9A and 9B show an alternative dynamic screw assembly that may be used with a plate-based inter-connecting member. The assembly employs a housing member 812 with an internal socket feature that accepts the complimentary spherical head 814 of bone screw 818. As before, partial members 812a and 812b are joined to form the assembled housing member 812 using threaded screws, but ratchets, clips, adhesives, or any other well-known technique for segment assembly may be alternatively used. The inner aspect of housing member 812 contains space that is positioned above the head 814. The space within the housing member 812 preferably contains a material or structure that resists movement of the bone screw head 814 relative to the inner aspect of the housing member 812. The assembly permits the orientation of member 812 to be freely adjustable relative to plate interconnecting member 820 (partially shown) before the assembly is locked. After deployment of locking nut 824, plate 820 is rigidly immobilized relative to housing member 812. However, screw 818 will remain mobile within the inner aspect of housing 812 as previously described in the embodiments of FIGS. 5 and 6.

Figure 10:
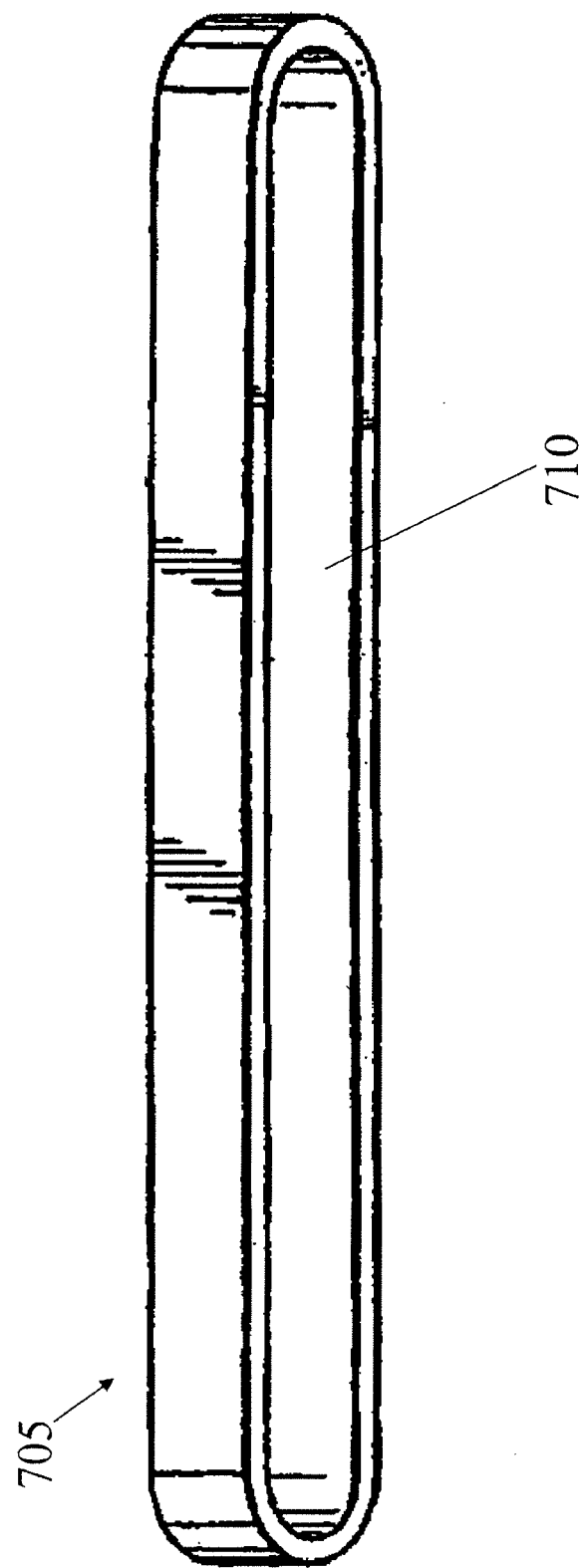
FIG. 10 shows an exemplary embodiment of a plate connector having an elongated slot for connecting to one or more bone screws.

In another embodiment, a loop or slotted plate connector is used in the cantilever framework in place of the rod. FIG. 10 shows an exemplary embodiment of a loop connector 705 having an elongated slot 710 for connecting to one or more bone screws. U.S. Pat. Nos. 6,083,224; 6,645,207; 6,682,530 and 6,884,241, which are incorporated herein by reference, demonstrate use of a slotted plate or similar loop connector member to interconnect bone screws. When connected to a rigid screw, the slotted plate or similar loop connector 705 provides the cantilever framework needed for stability while permitting dynamic screw translation along its long axis within slot 710. Alternatively, the dynamic screw of FIG. 9 may be used, for example, to provide rotational motion while maintaining the upper portion of the assembly stationary relative to connector 705. In this way, the connector 705 effectively functions like the rod shown in FIGS. 1-3. It should be appreciated that the rigid and dynamic screw assemblies disclosed herein are illustrative and that the method itself may be used with any rigid and dynamic fasteners.

The preceding disclosure described devices and methods through which alignment may be corrected and motion may be preserved even in those degenerated segments that currently require fusion and complete immobilization. In the foregoing method, a rigid screw and rod are used as a rigid cantilever framework onto which other vertebral segments may be attached using dynamic bone screw assemblies. Depending on the anchor site, the dynamic connectors may be attached on one side of the rigid cantilever framework or on both sides of it. In the cervical spine, for example, stability can be provided to a large segment of the neck by placement of a rigid bone screw in an intermediate level (usually C5) and then rigidly connecting it to a rod. This forms a cantilever framework onto which dynamic anchors can be attached. The dynamic screws are attached to an upper level (usually C2) and a lower level (usually C7 or T1) and, collectively, the construct provides effective stabilization the neck while preserving motion.

Any of the screw assemblies, inter-connectors and/or their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, the outer surface of the bone screw assemblies may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the screw assemblies, inter-connectors and/or any component can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method of vertebral stabilization, comprising:
affixing a first portion of a first bone fastener to a first vertebral bone;
coupling a second portion of the first bone fastener to a first portion of an interconnecting member, the interconnecting member further comprising at least a second portion configured to be at least partially contained within a first housing;
affixing a first portion of a bone fixation member to a second vertebral bone, the bone fixation member having a second portion configured to be at least partially contained within a second housing;
seating the first housing and the second portion of the interconnecting member contained therein within a first socket of an outer housing member;
seating the second housing and the second portion of the bone fixation member contained therein within a second socket of the outer housing member; and
transitioning a locking member from a first to a second state, the second state immobilizing each of the first housing and the second housing relative to the outer housing;
wherein each of the second portion of the interconnecting member and the second portion of the bone fixation member remain movable relative to the outer housing member when the locking feature is in both the first and the second state.

2. A method as in claim 1, further comprising attaching the second vertebral bone to the interconnecting member in a manner configured to permit movement between the second vertebral bone and the interconnecting member.

3. A method as in claim 1, further comprising attaching the second vertebral bone to the interconnecting member via a bone screw configured to permit dynamic movement between the interconnecting member and the second vertebral bone.

4. A method as in claim 1, wherein the first portion of the interconnecting member is movable relative to the second portion of the interconnecting member.

5. A method as in claim 1, wherein the interconnecting member comprises at least one rod segment, at least one plate segment, or at least one loop member.

6. A method as in claim 1, further comprising preventing movement between the first vertebral bone and the second vertebral bone in the anterior and posterior direction but permitting movement in all other directions.

7. A method as in claim 1, wherein the first vertebral bone comprises the sacrum and the second vertebral bone comprises a lumbar vertebra.

8. A method as in claim 1, wherein the second portion of the interconnecting member comprises a spherical end segment.

9. A method as in claim 8, further comprising articulating the second portion of the interconnecting member within the first housing via a ball-in-socket articulation thereof.

10. A method as in claim 1, further comprising utilizing a rod segment as the second portion of the interconnecting member, the rod segment configured to be movably contained within the first housing.

11. A method as in claim 1, further comprising moveably seating the second portion of the interconnecting member within the first housing and biasing the second portion of the interconnecting member towards an orientation relative to the first housing via a resilient member.

12. A method as in claim 1, wherein the second portion of the bone fixation member comprises a spherical end segment.

13. A method as in claim 12, further comprising articulating second portion of the bone fixation member within the second housing via a ball-in-socket articulation thereof.

14. A method as in claim 1, further comprising moveably seating the second portion of the bone fixation member within the second housing and biasing the second portion of the bone fixation member towards an orientation relative to the second housing via a resilient member.

15. A method as in claim 1, further comprising coupling the interconnecting member to the second vertebral bone via an intervening assembly comprising at least two ball-in-socked joints, such that each of the at least two ball-in-socket joints remains mobile when the locking member of the second bone fastener assembly is in any state.

16. A method as in claim 1, further comprising rigidly affixing the interconnecting member onto the first vertebral bone and extending the interconnecting member as a cantilever therefrom.

17. A method for dynamic fixation of a vertebral bone, comprising:
  affixing a first segment of a first bone fastener to a first vertebral bone;
  affixing a second segment of the first bone fastener to an interconnecting member;
  movably seating an end segment of the interconnecting member within a first housing;
  biasing the end segment of the interconnecting member towards an orientation relative to the first housing via a resilient member;
  attaching a first segment of a bone fixation member onto a second vertebral bone;
  seating at least a portion of the first housing within a first socket of an outer housing member, the end segment of the interconnecting member being at least partially contained within the first housing;
  seating at least a portion of a second segment of the bone fixation member within a second socket of the outer housing member; and
  transitioning a locking member from an unlocked to a locked state, the locking member configured to immobile the first housing relative to the outer housing when the locking member is in the locked state;
  wherein each the end segment of the interconnecting member and the second segment of the bone fixation member remain movable relative to the outer housing member when the locking member is in any state.

18. A method as in claim 17, wherein the end segment of the interconnecting member is spherical.

19. A method as in claim 18, further comprising articulating the end segment of the interconnecting member via a ball-in-socket articulation within the first housing.

20. A method as in claim 17, wherein the second segment of the bone fixation member comprises a spherical end segment.

21. A method as in claim 20, further comprising articulating the second segment of the bone fixation member via a ball-in-socket articulation within the outer housing.

22. A method as in claim 17, further comprising coupling the interconnecting member to the second vertebral bone via an intervening assembly comprising at least two ball-in-socked joints, such that each of the at least two ball-in-socket joints remains movable when the locking member is in any state.

23. A method as in claim 17, further comprising rigidly affixing the interconnecting member onto the first vertebral bone and extending the interconnecting member as a cantilever therefrom.

* * * * *